United States Patent
Zhang et al.

(10) Patent No.: US 7,495,552 B2
(45) Date of Patent: Feb. 24, 2009

(54) PRESCRIPTION-CUSTOMIZED MEDICAL HARDWARE

(75) Inventors: Tong Zhang, San Jose, CA (US); Steven John Simske, Fort Collins, CO (US); Daniel Robert Blakley, Philomath, OR (US); Charles Bruce, Rochester, MN (US); Paul Friedman, Rochester, MN (US); Virend Somers, Rochester, MN (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 566 days.

(21) Appl. No.: 11/107,127

(22) Filed: Apr. 15, 2005

(65) Prior Publication Data

US 2006/0253066 A1 Nov. 9, 2006

(51) Int. Cl.
*G08B 1/08* (2006.01)

(52) U.S. Cl. .................. 340/539.12; 340/521; 340/506; 600/300

(58) Field of Classification Search ............ 340/539.12, 340/573.1, 506, 521–522; 600/300; 705/2–3
See application file for complete search history.

(56) References Cited

U.S. PATENT DOCUMENTS

| | | | |
|---|---|---|---|
| 4,969,096 A | 11/1990 | Rosen et al. | |
| 5,704,366 A | 1/1998 | Tacklind et al. | |
| 5,897,493 A | 4/1999 | Brown | |
| 5,997,476 A | 12/1999 | Brown | |
| 6,080,106 A | 6/2000 | Lloyd et al. | |
| 6,336,900 B1 | 1/2002 | Alleckson et al. | |
| 6,368,273 B1 | 4/2002 | Brown | |
| 6,402,691 B1* | 6/2002 | Peddicord et al. | 600/300 |
| 6,454,705 B1 | 9/2002 | Cosentino et al. | |
| 2002/0103505 A1 | 8/2002 | Thompson | |
| 2003/0095648 A1* | 5/2003 | Kaib et al. | 379/106.02 |
| 2004/0199056 A1* | 10/2004 | Husemann et al. | 600/300 |

* cited by examiner

*Primary Examiner*—Daniel Wu
*Assistant Examiner*—Hongmin Fan

(57) ABSTRACT

A method of providing customized medical monitoring to a patient is disclosed. The method can include steps of selecting a medical monitoring device for a patient, where the medical monitoring device is associated with a biological transducer, determining at least one desired monitoring parameter, and customizing locally the medical monitoring device to monitor the desired monitoring parameter collected by the biological transducer. The method may further include steps of providing the medical monitoring device to the patient, and monitoring at least one health parameter of the patient from a remote location. The medical monitoring device can also be customized remotely.

31 Claims, 1 Drawing Sheet

PRESCRIPTION-CUSTOMIZED MEDICAL HARDWARE

FIELD OF THE INVENTION

The present invention relates generally to the medical monitoring of ambulatory patients. More particularly, the present invention relates to the customization of medical monitoring devices provided to a patient.

BACKGROUND OF THE INVENTION

Hospitals provide certain types of medical care to many patients that cannot be performed in a home environment. This is often the case with specific illnesses, surgeries, and other medical procedures that require a high level of monitoring of the patent. When medical conditions improve to the point that only occasional monitoring is required, patients can be released from the hospital or medical facility. For many patients, however, improvement can be a slow process that requires hospitalization for extended periods of time. These prolonged stays can become detrimental to the health of many patients. Unhealthy bacteria and viruses are often concentrated in a hospital environment, increasing many patients' risks of contracting associated illnesses and diseases in relation to the length of their stay. Also, prolonged stays in such an environment begin to affect the mental well-being of many patients. They often find it difficult to sleep, eat, and relax in such an environment. Similarly, monetary costs increase in relation to the length of the stay for patients, hospitals, and insurance providers.

As such, it is a benefit to all parties involved to discharge patients as soon as possible. In many cases, however, patients who would benefit from returning home are still in a condition that requires significant medical monitoring. Discharging patients in this condition may create health risks to the patients and liability for hospitals and insurance providers. One solution is to provide patients with remote medical monitoring devices. For example, a patient having a heart condition can be released from the hospital with a heart monitor. This allows the patient to be released to a more comfortable and/or familiar home environment while monitoring by the hospital continues. Through this device, the hospital can monitor the condition of the patient and take appropriate action when problems arise.

Current remote medical monitoring devices are limited in their usefulness, however, partially due to their generalist design. This "one size fits all" solution can be problematic, particularly for those patients that have medical conditions that do not quite match the design of the monitoring device. For such situations, medical care providers must often work around the limits of the device. Because of these limitations, medical care providers may keep patients longer in a hospital environment, or they may send them home with a limited device and risk further injury or even death, as well as increased liability.

It would thus be helpful to devise a means of providing patients with sufficient monitoring such that early releases from hospital environments are possible, while at the same time assisting medical care providers to provide patients with adequate monitoring to assure health safety.

SUMMARY OF THE INVENTION

It has been recognized that a method of providing customized medical monitoring to a patient would be advantageous. It would also be beneficial for the medical monitoring to be customizable to specific circumstances surrounding a patient's medical treatment. Specifically, a method for providing customized medical monitoring to a patient is disclosed. The method can include steps of selecting a customizable medical monitoring device for a patient, where the medical monitoring device is associated with a biological transducer, determining at least one intended health parameter, and customizing the medical monitoring device to monitor the at least one intended health parameter collected by the biological transducer.

In another embodiment of the present invention, a method for providing improved medical monitoring of a patient located at a remote location from a medical facility is disclosed. The method can comprise steps of providing a patient with a medical diagnosis and determining an appropriate modifiable medical monitoring device according to the medical diagnosis. Further steps include determining at least one intended health parameter related to the medical diagnosis, customizing the medical monitoring device to monitor the at least one intended health parameter, and providing the medical monitoring device to the patient. In accordance with embodiments of the present invention, an additional step of monitoring at least one health parameter of the patient via the medical monitoring device from a remote location can also be implemented.

Additional features and advantages of the invention will be apparent from the following detailed description which illustrates, by way of example, features of the invention.

BRIEF DESCRIPTION OF THE DRAWING

Features and advantages of embodiments of the present disclosure will become apparent by reference to the following detailed description and drawing.

DETAILED DESCRIPTION OF THE PREFERRED EMBODIMENTS

Figure 1:
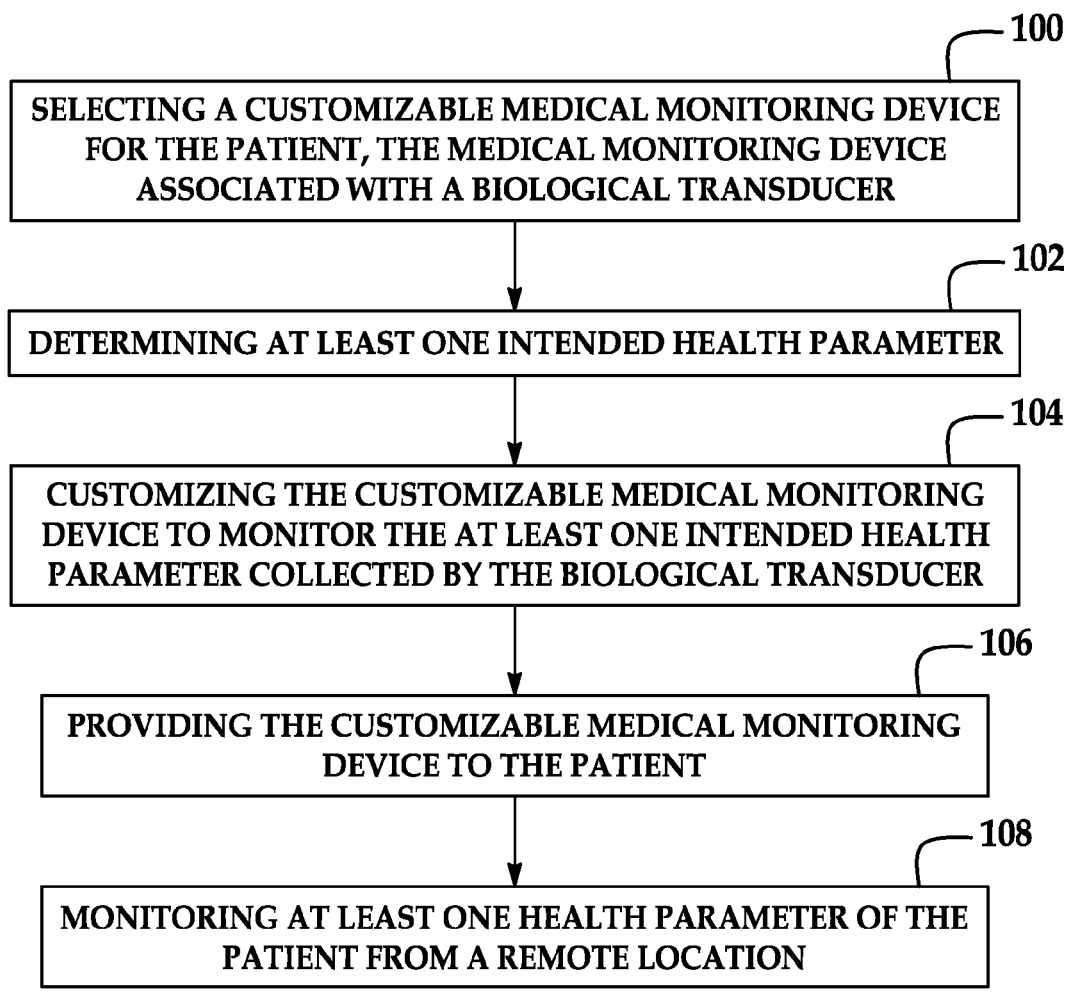
FIG. 1 is a schematic flow diagram depicting an embodiment of a method for providing customized medical monitoring of a patient to a medical care provider.

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a memory module" includes reference to one or more of such modules.

The term "medical monitoring device" refers to a device that collects and/or analyzes data received by the transducer, but does not include the transducer per se. In other words, the transducer is typically a peripheral device that is connected to the customizable medical monitoring device.

As used herein, the terms "customizing," "customized" and "customizable" can be used interchangeably, and refer to altering a medical monitoring device either remotely or locally. Such altering or alterations are intended to include not only physical changes of the hardware of the medical monitoring device, but also software changes. It is not intended, however, that alterations include a mere selection of transducers, such as leads or electrodes associated with the medical monitoring unit, or the mere adjustment of dials or switches on the device. For example, the term "customizable medical monitoring device" refers to medical monitoring devices that can be customized by an end user with minimal effort or expertise, e.g., loading software, changing a cartridge of memory, modifying a modular processor, adding a diagnostic module etc. A device requiring modification by a manufacturer would not be considered to be "customizable" in accordance with embodiments of the present invention.

As used herein, the terms "customizing locally" and "locally customized" can be used interchangeably, and refer to customization performed by an individual in the presence of the medical monitoring device.

The terms "customizing remotely" and "remotely customized" can be used interchangeably, and refer to customization performed by an individual who is not in the presence of the medical monitoring device.

The term "physiological waveform" refers to an analog or digital signal representation of a particular physiological activity. A physiological waveform can refer to a waveform of any given length. For example, physiological waveform can be an electrocardiogram (ECG) recorded over several hours, a sequential series of ECGs from a particular episode, a set of non-sequential normal or abnormal ECGs, a single ECG, or a portion of an ECG such as a QRS wave.

As used herein, the term "transducer" refers to a device utilized to transmit a physiological waveform or other biological data from the patient to the customizable medical monitoring device. In other words, a transducer as used herein can detect, transduce, and transmit a signal from the patient to the medical monitoring device. An example of a transducer can include leads to be used with an ECG monitor.

As used herein, the term "health parameter" refers to any aspect of a patient's physiology that can be monitored by a medical device. For example, a health parameter related to heart rhythms can include, without limitation, all ECG waves, normal ECG waves, abnormal ECG waves, a portion of an ECG wave such as the QRS wave, etc. Other health parameters include blood-sugar levels, $O_2$ levels, body weight, etc.

The term "medical care provider" refers to any individual providing medical care to an individual. This would include, for example, physicians, nurses, medical technicians, laboratory technicians, physicians' assistants, pharmacists, etc., but excludes manufacturers of medical equipment.

As used herein, the term "secondary medical condition" refers to medical conditions arising in a patient that are unrelated or somewhat peripherally related to the primary medical condition for which a patient is being monitored.

As used herein, the term "capacity" refers to total capacity. For example, increasing battery capacity would include increasing the total amount of battery power available. It would not include merely changing partially or totally discharged batteries for fully charged ones. Increasing battery capacity may thus entail estimating that the current battery capacity of a device is insufficient and choosing a battery with a greater power capacity.

The term "about" when referring to a numerical value or range is intended to encompass the values resulting from experimental error that can occur when taking measurements.

With these definitions in mind, it has been recognized that a method for customizing a medical monitoring device to more closely match a patient's specific medical monitoring needs would be an advancement in the art. It would also be beneficial for the medical monitoring device to be remotely customizable once it is in the possession of the patient.

FIG. 1 depicts an embodiment of the method for providing customized medical monitoring of a patient to a medical care provider. Generally, the method includes selecting a customizable medical monitoring device for the patient, the medical monitoring device associated with a biological transducer, as shown at reference numeral 100; determining at least one intended health parameter, as shown at reference numeral 102; customizing the customizable medical monitoring device to monitor the at least one intended health parameter collected by the biological transducer, as shown at reference numeral 104; providing the customizable medical monitoring device to the patient, as shown at reference numeral 106; and monitoring at least one health parameter of the patient from a remote location, as shown at reference numeral 108.

Embodiments of the present invention provide methods for customized medical monitoring that may allow early release of many patients from a hospital setting that would normally require in-hospital monitoring. These methods provide for a "hardware prescription" for reconfigurable hardware devices. Such prescription-customized medical hardware (PCMH) devices are thus individually customized to match a particular patient's monitoring needs, and thus function to monitor patients at remote locations from hospitals. The hardware prescription affords a medical care provider flexibility in managing patient care when the patient has left the direct care and supervision of a hospital, clinic, outpatient setting, or other medical facility. The hardware prescription can utilize a type of "recipe book" for conditional care that maps an initial prescription into the most likely future prescriptions of hardware according to a patient's conditions and needs. The idea behind such adaptive medicine is to provide customization of a patient's at-home medical care by mapping care requirements from a medical care provider into customized medical hardware, customized data collection, data analysis, and data storage associated with the PCMH.

In general, a customizable medical monitoring device can include a patient-utilized hardware device that has a different amount of memory, processing power, storage, and/or diagnostic module, based on the hardware prescription given to the patient. Further, customization is garnered from the tradeoff between firmware and interchangeable software modules that can be inserted or enabled into the device.

In one embodiment of the present invention, a method for providing customized medical monitoring to a patient is provided. The method can include steps of selecting a customizable medical monitoring device for a patient, where the medical monitoring device is associated with a biological transducer, determining at least one intended health parameter, and customizing (locally or remotely) the medical monitoring device to monitor the at least one intended health parameter collected by the biological transducer.

The selection of the medical monitoring device can be based on the medical condition of the patient. Any medical monitor known to one skilled in the art is considered to be within the scope of the present invention. For example, for a patient having a heart condition, some type of heart monitor may be selected. For a patient having asthma, some type of spirometer may be selected. It is also considered to be within the scope of the present invention for the selection of the medical monitoring device to include the selection of a generalized medical monitoring device that attains various general health monitoring functionalities depending on its customization parameters. For example, a generalized medical monitoring device may comprise electronics and a chassis configured to accept and integrate the functionality of various monitoring and diagnostic modules.

It should be understood that the selection of the medical monitoring device may not necessarily be made by the medical care provider assessing the patient's medical condition. In some cases, the medical care provider may even be unaware of the selection procedure, having written up a diagnosis or a prescription that provides only general medical details of the condition. Other medical care providers, on the other hand, may be personally involved in the selection of the medical monitoring device, and even in its subsequent customization. In other words, the level of involvement of the medical care provider in the steps of the various methods disclosed herein may be highly variable, often depending on their technical expertise in medical monitoring devices.

When a patient in need of monitoring is sent to a location remote from a hospital or other medical facility, various health parameters can potentially be monitored. In order to customize the medical monitoring device as closely to the individual needs and circumstances of a patient as possible, it is helpful to determine which health parameters would be linked to the medical condition of the patient in such a way as to provide useful indicators of the patient's health. A health parameter is thus merely a manifestation of a physiological process that is in some way indicative of some aspect of the health of the patient. The health parameter can be an objective measurement such as an ECG or a blood pressure reading, or it can be a subjective determination such as an indication from the patient that they feel light-headed. Also, the intended health parameter can be at least partially related to the diagnosis of the individual, or as discussed further below, in can be at least partially unrelated.

An intended health parameter can be determined at various levels. In one aspect, the intended health parameter can be determined through a hardware prescription communicated by the medical care provider. As with the selection of the customizable medical monitoring device, the level of involvement of the medical care professional in the determination of intended health parameters can be highly variable, depending on various factors, including level of expertise, time constraints, etc. Various means of assisting in this determination are available, regardless of the involvement of the medical care provider. In one aspect, a checklist for a particular medical condition can be utilized to suggest potential intended health parameters. This checklist can allow a medical care provider to check off specific intended health parameters to include in the medical monitoring device. For example, and without limitation, a checklist for heart related medical conditions can include customization suggestions for data compression techniques, specific hardware needs, sensors to be used, and the type of diagnosis monitored, such as atrial fibrillation, congestive heart failure, premature ventricular contraction, etc. It should be noted that a checklist can be physical, i.e., paper-based, or digital, e.g., PDA, digital pen, computer-based, etc. Also, the checklist may or may not be technical in nature. For example, one type of checklist may provide suggested hardware, software, compression techniques, etc. Another type may provide more mundane suggestions, such as the ambulatory level of the patient, the quality of the stored data, the amount of data to save, etc. Hardware could then be selected based on these more mundane suggestions. It is also contemplated that a suggested checklist could be provided to the medical care provider for their acceptance. These checklists can also be crafted and stored for future use with patients with similar medical conditions.

The selection of intended health parameters may also be based on a prior medical history of the patient. It may be useful to include an intended health parameter related to secondary medical conditions that have arisen in the past. Also, the selection can also include intended health parameters related to medical conditions that the medical care professional believes may arise, or desires to monitor in order to have advance warning of subsequent medical issues.

The intended health parameter can be selected at any scale recognizable to one skilled in the art. For example, the intended health parameter can be heart rate, the timing of contractions of the heart, or a particular sequence of the contraction cycle. Through the selection of these particular intended health parameters, a medical monitoring device can be constructed to monitor heart rate, ECG waveforms, or specific sections of ECG waveforms, respectively. Thus, it is contemplated that intended health parameters also include portions of physiological waveforms, such as the QRS portion of the ECG waveform. Intended health parameters can also include specific types of data selected from an overall group. For example, the medical care provider can specify that the intended health parameter is "all abnormal ECGs", and thus, normal ECGs can be discarded or compressed to conserve space in the medical monitoring device, while abnormal ECGs be left uncompressed and either stored on the device or sent directly to a medical monitoring facility.

Medical monitoring devices can then be customized to monitor at least one intended health parameter. Customizing can include any software or hardware changes to the medical monitoring device made for the purposes of health monitoring based on the specific needs of the patient. This would not include mere adjustments of the settings or dials of a device, or the mere selection of transducer types, such as leads for an ECG monitor. For example, the process of customizing can be that which is easily carried out by the health care provider, but should not be easily carried out by the patient without the health care provider's instruction or consent. Switching modules that are available to the heath care provider is an example of a parameter that is easily modifiable by a health care provider, but would not be easily carried out by the patient due the patient's inaccessibility to the appropriate equipment or modules. The patient may also not have "security access" to their own data due to safety and legal concerns. This being said, the patient can carry out or initiate such modifications under the direction of the health care provider in certain embodiments of the present invention.

As previously mentioned, customizing can be performed locally or remotely. It is intended that customizing locally includes customization that is performed by an individual in the presence of the medical monitoring device. This would include, for example, modifications made by a technician in possession of the device, or modifications made by the patient in possession of the device upon instruction and permission from the medical care provider. It is intended that customizing remotely includes customization that occurs when the medical monitoring device is not in the immediate presence of the health care provider. This would include, for example, uploading software to, or enabling software already on the device when it is in the possession of the patient at a remote location by an individual not present at that location. This can be carried out by connecting the device to a network for remote modification, or by receiving instructions from the health care provider to change a module, for example. Patient access to software registry and permission to alter the configuration may be controlled by security software under privilege of the medical care provider's organization.

In one aspect of the present invention, a customizable medical monitoring device can be customized locally to monitor at least one intended health parameter to be collected by the biological transducer. Several general categories of local customization provide various levels of functionality to a particular medical monitoring device, though customizations outside of these areas would be considered to be within the scope of the present invention.

A medical monitoring device can be customized locally in order to modify its data acquisition or data analysis functionality. In one aspect of the present invention, customizing can include altering the amount of control, program, cache, or storage memory within the device. These types of memory are well known in the art, and will thus not be discussed fully herein. It is intended that the term altering include increasing or decreasing the total amount of physical memory available. Various combinations of total amounts of each type of physical memory can generate medical monitoring devices having disparate data processing functionalities. For example, in situations where there may be little or no data analysis occurring on the medical monitoring device, it can be locally customized to include increased storage memory and have less program memory. In situations where data will be analyzed and only a portion retained for upload to the medical care facility, the medical monitoring device can be customized locally to include increased program and control memory and have less storage memory.

In another aspect of the present invention, customizing locally in order to modify data acquisition and data analysis functionality can also be accomplished by altering the processing power of the medical monitoring device. This can be accomplished by switching a processing unit for one of higher or lower processing capability, or by adding additional processing units to the medical monitoring device. Altering processing power can also be accomplished by utilizing a processing unit that functions at various processing speeds. For these units, processing speed can be lowered when it is not required in order to conserve battery time and reduce heat generation, and increased for those circumstances requiring higher processing power.

In another aspect of the present invention, a medical monitoring device can be customized locally in order to more effectively monitor a particular medical condition. In such cases, data modules can be added to the medical monitoring device in order to monitor particular aspects of a patient's physiology. These data modules may analyze or record particular portions of a waveform, or perform specific diagnostic functions on waveform data or biological fluids. It is also contemplated that diagnostic modules can be added to the device in order to monitor and diagnose potential aspects of a medical condition. The overall functionality of the medical monitoring device can thus be changed based on the addition of various monitoring and/or diagnostic modules. It should be understood that a module can be a physical hardware device, or it can be software. In the latter case, the software can be uploaded to the device or it may already be resident on the device and merely need to be enabled. It is also contemplated that physically interchangeable software modules could be added to the medical monitoring device in order to modify available software. Software contained in modules that is not needed for a particular patient can be removed from the medical monitoring device, if present. For example, and without limitation, a medical monitoring device customized locally for a patient being monitored for atrial fibrillation may contain modules for atrial fibrillation, ventricular escape, premature ventricular contraction, and other possible downstream heart disorders that are likely if the atrial fibrillation worsens.

In one embodiment, a biological parameter module can be can be added which is attached or tethered to a biological or chemical sensor or transducer. The module can be added to alter the functionality of the medical monitoring device. These modules and associated sensors/transducers can detect electrical signals, or take measurements from biological fluids or solids. Examples of useful, changeable modules can include, without limitation, modules attached to oxygen saturation sensors, blood pressure sensors, heart rate sensors, blood glucose sensors, urinalysis sensors, thermometers, skin impedance meters, accelerometers/motion detectors, voice recorders, etc. Biological parameter modules including associated sensors can be added that may be unrelated to the primary medical condition. For example, a patient with a heart condition might have a medical monitoring device with primarily heart-related functions but that also includes a blood glucose module with an associated sensor due to a diabetic condition.

In another aspect of the present invention, the medical monitoring device can be customized locally to accommodate the probable ambulatory activity of a patient. More active patients may require devices having larger memory storage and a greater battery capacity to accommodate for longer periods away from an aggregator or other communication means. Similarly, data compression algorithms can be altered in order to increase the amount of data that can be stored while away from a means of uploading data.

In one embodiment, the customization can be carried out locally, and then modified remotely. For example, once the medical monitoring device has been customized locally, it can be provided to the patient, and at least one health parameter of the patient can be monitored from a remote location. The health parameter can be a single or multiple health parameters. A health parameter can include the intended health parameter for which the medical monitoring device was customized locally. It can also include a parameter that is peripherally related or unrelated to the intended health parameter. In some cases the medical monitoring device may be used to monitor a health parameter that is somewhat outside of the scope of what was originally intended for a patient.

The monitoring of a patient can occur via any communication means known to one skilled in the art. This can include, without limitation, the Internet, local area networks, cellular networks, telecommunication networks, cable networks, digital satellite networks, dedicated telecommunication lines, satellite links, etc. If the bandwidth between the patient and the medical care provider is low but there is ample patient-side physical data storage, mailing of physical media from the patient to the medical care provider is also contemplated. It is intended that two-way communication be established between the medical care provider and the patient being monitored. The two-way communication can utilize the same communication means in both directions, or it may utilize different communication means in each direction. For example, two-way communication can be accomplished solely via an Internet connection, or it can be accomplished by a combination of Internet and cellular network connections. Communication networks are well known to those skilled in the art, and as such they will not be discussed in detail herein.

One advantage of two-way communication is that it allows the customizable medical monitoring device to be customized remotely. As mentioned herein, customizing remotely includes any modification to the customizable medical monitoring device made by an individual who is not physically present with the device when the modification occurs. Any type of customization or modification that can occur remotely is considered to be within the scope of the present invention. In one aspect of the present invention, customizing remotely can include uploading software to the customizable medical monitoring device. The uploading of software can occur over the communication means utilized to monitor the patient, or a new connection or type of communication means can be initiated for the upload. In another embodiment, customizing remotely can include enabling or disabling software already resident on the medical monitoring device. In yet another aspect of the present invention, customizing remotely can include enabling or disabling hardware modules present on the device in order to modify the functionality of the customizable medical monitoring device.

In one aspect, customizing remotely can occur as a result of a change in the patient's health or a monitored health parameter. For example, as the monitoring needs of the patient extend outside of the monitoring capability of the medical monitoring device, remote customization can modify the devices functionality to include these additional monitoring needs. Software and hardware not being currently used to monitor the patient's health can be inactivated or deleted from memory in order to conserve power and memory space. For example, if a patient progresses from atrial fibrillation to ventricular escape, the digital sampling rate of the medical monitoring device may be decreased and multiple leads recorded to help the medical care provider diagnose the injury current and/or cardiac vector. In such a case, other sampling or monitoring may be disabled.

In another aspect, customizing remotely can occur due to changes in a patient's medication regimen. Changes in medication often can increase certain health risks. When a patient changes medication, remote customization of the medical monitoring device can occur in order to allow the device to monitor health parameters that may give advance warnings of medication related issues. As an example, if the patient is newly treated for cluster headaches with calcium blockers, the medical care provider may want to monitor blood pressure to make sure it doesn't drop too suddenly or too severely.

In yet another aspect, customizing remotely can occur in order to collect diagnostic medical data. Altering remotely the functionality of the medical monitoring device may be helpful in situations where additional diagnostic data would be helpful without resorting to returning the patient to the hospital or medical care facility. Diagnostic software can be uploaded or activated to monitor and collect data pertaining to additional health parameters or specific aspects of a particular health parameter.

It is to be understood that the above-referenced arrangements are illustrative of the application for the principles of the present invention. Numerous modifications and alternative arrangements can be devised without departing from the spirit and scope of the present invention while the present invention has been described above in connection with the exemplary embodiments(s) of the invention. It will be apparent to those of ordinary skill in the art that numerous modifications can be made without departing from the principles and concepts of the invention as set forth in the claims.

What is claimed is:

1. A method of providing customized medical monitoring of a patient to a medical care provider, comprising steps of:
    selecting a customizable medical monitoring device for the patient, the medical monitoring device associated with a biological transducer;
    determining at least one intended health parameter;
    customizing the customizable medical monitoring device according to at least one of a hardware prescription from the medical care provider, firmware or interchangeable software modules to monitor the at least one intended health parameter collected by the biological transducer;
    providing the customizable medical monitoring device to the patient;
    monitoring at least one health parameter of the patient from a remote location; and
    reconfiguring either locally or remotely at least one patient-utilized hardware device of the customizable medical monitoring device according to the at least one of the hardware prescription from the medical care provider, the firmware or the interchangeable software modules;
    wherein when the reconfiguring is based on the hardware prescription, the hardware prescription maps from an initial hardware prescription to a selection of contingent hardware prescriptions, and the hardware prescription for the reconfiguring is selected as needed from the initial and contingent hardware prescriptions according to the patient's changing conditions and needs;
    wherein the at least one patient-utilized hardware device of the customizable medical monitoring device is selected from the group consisting of memory, processing power, storage, and diagnostic module.

2. The method of claim 1, wherein the step of customizing includes customizing locally the customizable medical monitoring device.

3. The method of claim 1, wherein the step of customizing includes customizing remotely the customizable medical monitoring device.

4. The method of claim 3, wherein the step of customizing remotely includes uploading software to the customizable medical monitoring device.

5. The method of claim 3, wherein the step of customizing remotely includes enabling or disabling software in the customizable medical monitoring device.

6. The method of claim 3, wherein the step of customizing remotely occurs due to changes in the at least one health parameter.

7. The method of claim 3, wherein the step of customizing remotely occurs due to changes in a medication regimen of the patient.

8. The method of claim 3, wherein the step of customizing remotely occurs in order to collect diagnostic health data.

9. The method of claim 1, wherein the intended health parameter includes a portion of a physiological waveform.

10. The method of claim 2, wherein the step of customizing locally further includes a step of adding a data module to the customizable medical monitoring device.

11. The method of claim 10, wherein the data module performs data analysis.

12. The method of claim 2, wherein the step of customizing locally further includes a step of altering an amount of control memory in the customizable medical monitoring device.

13. The method of claim 2, wherein the step of customizing locally further includes a step of altering an amount of program memory in the customizable medical monitoring device.

14. The method of claim 2, wherein the step of customizing locally further includes a step of altering an amount of storage memory in the customizable medical monitoring device.

15. The method of claim 2, wherein the step of customizing locally further includes a step of altering processing power of the customizable medical monitoring device.

16. The method of claim 2, wherein the step of customizing locally further includes a step of altering software in the customizable medical monitoring device.

17. The method of claim 16, wherein the step of altering software further includes a step of adding an interchangeable software module to the customizable medical monitoring device.

18. The method of claim 2, wherein the step of customizing locally further includes a step of altering data compression within the customizable medical monitoring device.

19. The method of claim 2, wherein the step of customizing locally further includes a step of altering battery capacity of the customizable medical monitoring device.

20. The method of claim 1, wherein the biological transducer is changeable.

21. The method of claim 20, wherein the biological transducer measures a biological fluid.

22. The method of claim 2, wherein the step of customizing locally includes a step of adding a medical diagnostic module to the customizable medical monitoring device.

23. The method of claim 1, wherein the step of determining the at least one intended health parameter at least partially depends on a prior history of the patient.

24. The method of claim 1, wherein the intended health parameter is at least partially related to the diagnosis of the patient.

25. The method of claim 1, wherein the intended health parameter is at least partially unrelated to the diagnosis of the patient.

26. The method of claim 1, wherein the customizable medical monitoring device is at least partially customized by the patient.

27. The method of claim 1, wherein the at least one health parameter is the at least one intended health parameter.

28. A method for providing improved medical monitoring of a patient located at a remote location from a medical facility, comprising steps of:
providing the patient with a medical diagnosis;
determining an appropriate customizable medical monitoring device according to the medical diagnosis;
determining at least one intended health parameter related to the medical diagnosis;
providing the medical monitoring device to the patient;
customizing the medical monitoring device according to at least one of a hardware prescription from the medical care provider, firmware, or interchangeable software modules to monitor the at least one intended health parameter;
monitoring at least one health parameter of the patient via the medical monitoring device from a remote location; and
reconfiguring either locally or remotely at least one patient-utilized hardware device of the customizable medical monitoring device, the reconfiguring being based on the at least one of the hardware prescription, the firmware, or the interchangeable software modules;
wherein when the reconfiguring is based on the hardware prescription, the hardware prescription maps from an initial hardware prescription to a selection of contingent hardware prescriptions, and the hardware prescription for the reconfiguring is selected as needed from the initial and contingent hardware prescriptions according to the patient's changing conditions and needs;
wherein the at least one patient-utilized hardware device of the customizable medical monitoring device is selected from the group consisting of memory, processing power, storage, and diagnostic module.

29. The method of claim 28, further including a step of determining at least one intended health parameter related to a prior medical history of the individual.

30. The method of claim 28, further comprising a step of customizing remotely the medical monitoring device.

31. The method of claim 30, wherein the step of customizing remotely occurs due to changes in the at least one health parameter.

* * * * *